US00PP09073P

United States Patent [19]

Moser

[11] Patent Number: Plant 9,073

[45] Date of Patent: Mar. 14, 1995

[54] AZALEA PLANT NAMED SINCERITY

[75] Inventor: Frank C. Moser, Alva, Fla.

[73] Assignee: Yoder Brothers, Inc., Barberton, Ohio

[21] Appl. No.: 223,855

[22] Filed: Apr. 6, 1994

[51] Int. Cl.[6] ..... A01H 5/00

[52] U.S. Cl. ..... Plt./57

[58] Field of Search ..... Plt. 55, 56, 57

*Primary Examiner*—James R. Feyrer

*Attorney, Agent, or Firm*—Foley & Lardner

[57] ABSTRACT

An azalea plant named Sincerity, particularly characterized by its dark rose pink flower color, large ruffled double hose-in-hose flower form, free branching, uniform and spreading plant habit, uniform flowering response in a year round controlled program, and excellent cooler tolerance and keeping quality.

1 Drawing Sheet

The present invention comprises a new and distinct cultivar of Azalea, a greenhouse forcing type, hereinafter referred to as Sincerity.

Sincerity, identified as Code 857 during the selection process, originated from a planned cross hybridization between two selected breeding lines in a controlled breeding program in Fort Myers, Fla. by the inventor Frank C. Moser.

The female, or seed parent of Sincerity is the commercial cultivar Ikon, a dark rose red semi-double hose-in-hose with a compact habit and glossy dark green foliage, and disclosed in U.S. Plant Pat. No. 6,607. The male, or pollen parent is a seedling known as Code 227, a proprietary breeding line.

Sincerity was discovered and selected as one flowering plant within the progeny of the stated cross by the inventor Frank C. Moser in October 1988, in Fort Myers, Fla.

The first asexual reproduction of Sincerity was accomplished when vegetative cuttings were taken from the initial selection in December 1988, in Fort Myers, Fla., by technicians working under formulations established and supervised by Frank C. Moser.

Horticultural examination of controlled flowerings of successive generations of plants derived from cuttings taken from the original selection has shown that the unique combination of characteristics as herein disclosed for Sincerity are fixed and retained through successive generations of asexual reproduction.

Sincerity has not been observed under all possible environmental conditions. The phenotype may vary significantly with variations in environment such as temperature, light intensity and day length, without, however, any variance in the genotype.

The following observations, measurements and comparisons describe plants that were grown in Fort Myers, Fla. in a controlled greenhouse environment and following a commercial schedule.

The following traits have been repeatedly observed and are determined to be basic characteristics of Sincerity, which in combination distinguish this azalea as a new and distinct cultivar:

1. A dark rose pink flower color (57B) upon opening, fading to a lighter pink color (57D) as flowers age.

2. Semi-double to double flowers with a ruffled margin, with the flowers ranging from 7.0 to 9.0 cm in diameter, with 8.0 cm the average size.

3. Compact, spreading and freely branching plant habit.

4. Uniform response in year round controlled flowering programs, forcing in 31 days on average.

5. Long lasting flowers, with flowers in a simulated home environment lasting up to 25 days.

6. Medium green glossy evergreen foliage, leathery in appearance.

7. Very good foliage retention and no flower bud damage when cooled for 6 weeks with no light at 38° F.

The accompanying color photograph shows in perspective view the unique features of the new cultivar, with colors being as true as possible with color illustrations of this type.

Of the commercial cultivars known to the inventor, the most similar in comparison to Sincerity is the variety Prize, disclosed in U.S. Plant Pat. No. 3,795. Flower color and flower response are very much alike.

Sincerity differs from Prize in that Sincerity has ruffled petal margins and larger flowers than Prize. The foliage of Prize appears to be smoother and darker green than that of Sincerity, and the shape of Prize foliage is obovate compared to the foliage of Sincerity which is closer to elliptic in shape. Plants of Sincerity tend to be more spreading and less upright than those of Prize.

In the following description color references are made to The Royal Horticultural Society Color Chart. The color values were determined on Feb. 15, 1994. All readings were taken in an office under cool while fluorescent lights, facing a west window between the hours of 10:00 a.m. and 2:00 p.m.

Classification:

*Botanical.*—Rhododendron hybrida, evergreen type.

*Commercial.*—Florist forcing post azalea.

INFLORESCENCE

A. Flower (general):

*Size.*—7.0 to 9.0 cm.

*Borne.*—Terminal cluster, usually 2 per bud, ranging from 1-3. Often more than one bud per stem.

*Form.*—Semi-double to double hose-in-hose. Funnelform.

*Blooming habit.*—Once, profusely. Buds easily and uniformly in a year round flowering program. The majority of terminal buds break color within one week of the first. Flowering begins approximately 31 days after the start of forcing.

*Fragrance.*—none.

B. Corolla (petals):

*Texture.*—Soft.

*Substance.*—Heavy.

*Shape.*—Rounded. Margins undulate.

*Color (fully open).*—Generally 57B, dark rose pink, fading to 57D as flowers age. Upper surface: Edge: 57B. Center: 57B. Base: 49B. Lower surface: 57C to 48A. Blotch: 60B.

C. Bud:

*Size.*—Medium.

*Shape.*—Conoidal.

*Color.*—58C.

*Bud sheath.*—Light green with light brown hairs.

D. Calyx:

*Form.*—Petaloid, irregular shape lacking symmetry, margin irregular and undulate.

*Color.*—Upper surface: 57B. Lower surface: 58C.

E. Peduncle:

*Length.*—0.7–1.5 cm.

*Strength.*—Strong.

*Aspect.*—Pubescent.

F. Reproductive organs:

*Androecium (stamens).*—Number: Usually 5 to 10. Some partially transformed into petals, some are fused with the style. Anthers: 58B. Filaments: Length: 0.5 to 3.0 cm. Color: 58C.

*Gynoecium (pistil).*—Stigma: 46A. Style: Length: 2.2–3.5 cm. Color: 45C. Ovary: Pubescent.

PLANT CHARACTERISTICS

A. Foliage:

*Type.*—Evergreen.

*Arrangement.*—Alternate.

*Shape.*—Elliptic, apex mucronate to mucronulate, base acute to attenuate.

*Size.*—Length: 2.0–7.5 cm. Width: 1.2–3.5 cm.

*Margin.*—Entire.

*Color.*—Immature: Upper suface: Between 144A and 146A. Mature: Upper surface: 139A. Lower surface: 146B.

*Texture.*—Leathery.

*Tomentum.*—Present on upper surface. Insignificant.

B. Stems:

*Color.*—Immature: 145B. Mature: 165A. Tomentum: 164A.

C. Plant habit: Compact, spreading bush which achieves a uniform, symmetrical plant in a six-inch pot when pinched three times. Total crop time to the dormant budded stage is 40–42 weeks to produce a plant approximately 30–38 cm in diameter and a total height of 26–34 cm. Internode lengths vary widely from 2 to 25 mm on the same stem.

D. Branching habit: Free branching, producing 3 to 4 breaks when a vegetative cutting is pinched.

E. Rooting: Roots easily in 8 to 10 weeks with 75° F. soil temperature.

F. Budding ease: Plants produce flower buds easily and uniformly year round with the use of commercially available plant growth regulators. Natural season response has not been ascertained.

G. Cooler tolerance: Plants placed in a cooler as a means of breaking dormancy perform very well. Sincerity is tolerant of six weeks in an unlighted cooler at 38° F. without foliage loss or bud damage.

H. Blooming: Plants reach the stage of 12 buds showing color in 31 days on average after the cooling treatment. This varies from 15 to 42 days depending upon temperature and stage of flower bud development at the start of forcing. Sincerity flowers uniformly across the plant.

I. Shelf-life: When plants are moved to an office or home environment at the stage of eight open flowers, they maintain an attractive appearance for 25 days on average. Flowers are somewhat persistent, only occasionally dropping as flowers become old.

I claim:

1. A new and distinct cultivar of azalea named Sincerity, as described and illustrated.

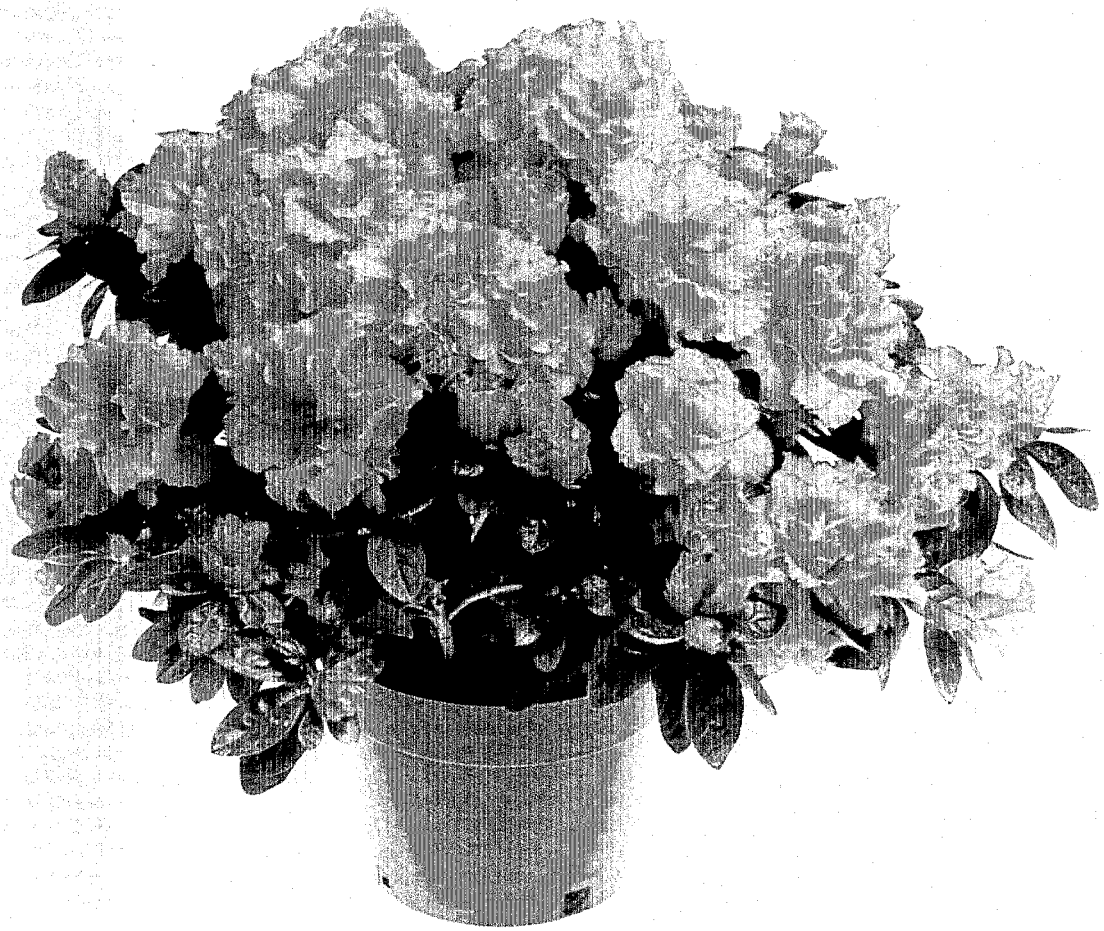

* * * * *